(12) United States Patent
Hau et al.

(10) Patent No.: US 10,049,263 B2
(45) Date of Patent: Aug. 14, 2018

(54) COMPUTER-BASED MICRO-EXPRESSION ANALYSIS

(71) Applicant: Stephan Hau, Stockholm (SE)

(72) Inventors: Stephan Hau, Stockholm (SE);
Lennart Högman, Stockholm (SE);
Håkan Fischer, Stockholm (SE)

(*) Notice: Subject to any disclaimer, the term of this patent is extended or adjusted under 35 U.S.C. 154(b) by 0 days.

(21) Appl. No.: 15/183,622

(22) Filed: Jun. 15, 2016

(65) Prior Publication Data
US 2017/0364741 A1 Dec. 21, 2017

(51) Int. Cl.
*G06K 9/00* (2006.01)
*H04N 5/247* (2006.01)
*G10L 15/26* (2006.01)
*G10L 15/18* (2013.01)
*A61B 5/00* (2006.01)

(52) U.S. Cl.
CPC ........ *G06K 9/00302* (2013.01); *A61B 5/0077* (2013.01); *G10L 15/1815* (2013.01); *G10L 15/26* (2013.01); *H04N 5/247* (2013.01)

(58) Field of Classification Search
CPC .............. G06F 17/2785; G06F 17/28; G06F 2203/011; G06F 3/013; G06F 3/015; G06K 9/00; H04N 21/44218
See application file for complete search history.

(56) References Cited

U.S. PATENT DOCUMENTS

| | | | |
|---|---|---|---|
| 9,741,258 B1* | 8/2017 | Chetlur | G09B 5/12 |
| 2012/0002848 A1* | 1/2012 | Hill | A61B 5/164 |
| | | | 382/118 |
| 2013/0103624 A1* | 4/2013 | Thieberger | G06N 99/005 |
| | | | 706/12 |
| 2014/0108309 A1* | 4/2014 | Frank | G06N 99/005 |
| | | | 706/12 |
| 2014/0108842 A1* | 4/2014 | Frank | G06F 17/28 |
| | | | 713/323 |
| 2014/0149177 A1* | 5/2014 | Frank | G06Q 10/06 |
| | | | 705/7.29 |
| 2015/0271571 A1* | 9/2015 | Laksono | H04N 21/44222 |
| | | | 725/14 |
| 2016/0042648 A1* | 2/2016 | Kothuri | G06F 3/015 |
| | | | 434/236 |
| 2016/0306870 A1* | 10/2016 | Yoselis | G06K 9/00 |
| 2016/0345060 A1* | 11/2016 | Marci | H04N 21/44218 |

* cited by examiner

*Primary Examiner* — Li Liu
(74) *Attorney, Agent, or Firm* — Fish & Richardson P.C.

(57) ABSTRACT

A computer-implemented method of digital image analysis includes obtaining first digital video of a human subject that indicates facial expressions of the human subject; performing micro-expression analysis on the human subject using the first digital video; comparing results of the performed micro-expression analysis with content of a presentation determined to have been provided to the human subject at the same time that particular portions of the digital video were initially captured; and modifying a manner of performing interaction with the human subject or other human subjects based on the comparing of results.

20 Claims, 4 Drawing Sheets

COMPUTER-BASED MICRO-EXPRESSION ANALYSIS

TECHNICAL FIELD

This document generally describes technology related to computer-based automated analysis of human facial responses coordinated with analyzed verbal and visual inputs.

BACKGROUND

Micro-expression refers to brief, involuntary facial expression shown by a person that indicate emotions currently being experienced by such person. They may indicate subconscious responses by a person (thus indicating some reaction that the person does not even know that he or she is having) and can indicate the person's inner emotions even when the person is actively trying to hide emotions. Micro-expressions are very brief, typically on the order of 1/25 to 1/15 of a second. Micro-expressions may be interpreted in certain situations so as to classify the emotions of a person as one or more of emotional labels: disgust, anger, fear, sadness, happiness, contempt, surprise, amusement, embarrassment, anxiety, guilt, pride, relief, contentment, pleasure, and shame.

Micro-expressions have been sub-classified into three main groups according to how an expression is modified. First, "simulated expressions" are micro-expressions that are not accompanied by a genuine emotion (a brief flash of expression that then returns to a neutral state), which is the most commonly-studied form of micro-expression because of its nature. Second, "neutralized expressions" occur when a person suppresses a genuine expression and the face remains neutral, and is generally not observable because of its suppression. Third, "masked expressions" occur when a real expression is completely masked by a false expression.

SUMMARY

This document generally describes systems and techniques for digitally analyzing micro-expressions in video-captured images of a human subject, in timewise coordination with data that indicates information that is currently being presented to the human subject. For example, a series of frames of continuous images of a human patient may be captured as the patient is conversing with a psychotherapist, and micro-expression may be correlated with topics that the psychotherapist is raising in order to help the psychotherapist better shape the therapy. Data may be presented immediately to the psychotherapist, for example as textual descriptions on a portable computing device whose display can be viewed by the psychotherapist while the therapy session is occurring. Such textual descriptions may indicate that, for example, the topic is making the patient nervous, anxious, angry, or any other emotion label that can be applied using micro-expression analysis, and the psychotherapist may immediately correlate that feedback with the topic the psychotherapist was just most recently covering with the patient. The psychotherapist may then decide to go deeper into a topic if it indicates, for example, that the topic is creating minor discomfort for the patient, and avoid the topic if the analysis indicates that the patient is experiencing extreme discomfort. Other techniques for communicating the patient's micro-expression derived emotional state to the therapist may also be used, including by displaying graduated colors to the therapist, where, e.g., colors closer to green indicate general patient comfort and colors closer to red indicate general patient discomfort.

Such data may also be captured for later usage. For example, a therapist may select a topic from a menu before (or immediately after) discussing the topic with the patient, and a computing device of the therapist aligning time-correlated information derived from micro-expression analysis with the selected topic. In other examples, the topic can be determined by performing speech-to-text conversion on statements made by the psychotherapist and/or the patient (as captured by microphones and then digitized), and performing topical analysis on the text of those spoken words to identify topics covered in those discussions as compared to a transcript of a session. Those topics may then be time-aligned to micro-expression data obtained from video captured at the time of the making of the statements in the transcript. Particular emotion labels may then be associated with particular topics, either for a particular patient or across a large number of different patients.

Where such analysis occurs, the correlation of micro-expression data to topics may also be aggregated across many subjects (in this example, patients) of the micro-expression analysis. As one example, a researcher could interview many different human subjects using a common outline or script, and micro-expression analysis may be used to automatically discern patterns in response by groups of subjects to the topics raised by the researcher. The micro-expression data for each subject could be correlated with particular topics tied to particular parts of the script. And the micro-expression data may then be aggregated across different subjects for each such topic, and may be further correlated to other subject-specific data separately obtained, such as the age, gender, race, and background of the subject (e.g., current or prior professions/jobs, psychological diagnoses, and the like). For example, a researcher may interview a relatively large number of people who have combat military experience and a relatively large number who have no military experience, and may correlate the micro-expression results of each to particular discussion topics. As one example, such a study may reveal that people with combat experience have, on average, a micro-expression reaction of value X, on average, for a particular observed emotion, and people without have a reaction of value Y, on average.

A pair of video images may also be used to capture micro-expression data simultaneously on two subjects who are conversing with each other, or to determine visual cues of a signal that is being presented to a subject who is being analyzed. A pair of cameras, each aimed at a respective subject, may be used to capture the video, or one video stream may come from a signal (e.g., a television feed) and the other may come from a local camera aimed at a subject who is watching the first video stream. For example, a manager may be trained to interact better with potential employees or actual employees by capturing video of the manager to identify emotional tags the manager is visually expressing (via micro-expression analysis) and by capturing video of the employee or potential employee to determine how, emotionally, they are reacting—with the ability to correlate the interviewee's reaction to non-micro-expression or micro-expression aspects of the interviewer's presentation. Such analysis may provide the manager with immediate feedback that is automatically delivered by a computer system and thus may be viewed by the manager as being more objective in its measurements than would comments from a human observer of the manager's interaction.

In one implementation, a computer-implemented method for digital image analysis is disclosed. The method comprises obtaining first digital video of a human subject that indicates facial expressions of the human subject; performing micro-expression analysis on the human subject using the first digital video; comparing results of the performed micro-expression analysis with content of a presentation determined to have been provided to the human subject at the same time that particular portions of the digital video were initially captured; and modifying a manner of performing interaction with the human subject or other human subjects based on the comparing of results. The method may further comprise obtaining second digital video of a presentation with which the human subject was interacting when the first digital video was captured; and time-wise aligning data generated from the second digital video with the results of performing the micro-expression analysis, so that particular ones of the results of performing the micro-expression analysis are correlated with particular messages delivered by the presentation to the human subject.

In certain aspects, the presentation with which the human subject interacts can be a conversation with another human. The method can also comprise converting speech by the another human to text for computer analysis. Moreover, the method can include electronically identifying one or more topics to which text from speech of the another human is determined to be directed. In addition, the method may comprise electronically correlating each of the identified one or more topics to corresponding emotion tags identified from the micro-expression analysis that indicate emotional reactions of the human subject to the one or more topics.

In certain implementations, the systems and techniques discussed here may provide one or more advantages. For example, dialogue interactions may be studied via computers (with automatic micro-expression data generation) to identify actions that have particularly positive or negative reactions from a human subject. Such analysis may allow for the improvement of such interactions, such as by a psychotherapist immediately seeing feedback that a particular line of questioning is having a negative effect on a patient, so that the therapist can change a therapy approach immediately, or by analyzing a dialogue approach after-the-fact to improve future use of the approach, such as by changing the text of a script that is used to drive the dialogue—and where such analysis may be focused on a single human subject or a large group of subjects whose micro-expression reactions are analyzed, and then aggregated to identify appropriate dialogue approaches to use with groups of people in the future. Where multiple subjects are analyzed, they can be subjected to the dialogue individually, or in a group (where separate cameras may be trained on the faces of the different subjects in a room or a single high-resolution video image may capture all the subjects).

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

This document generally describes techniques for automatically correlating a human subject's emotions, as exhibited through micro-expressions and automatically identified electronically, with current stimuli that are being provided to the human subject in a dialogue session. The dialogue session may include, for example, another person talking to the human subject, such as a therapist or interviewer/interviewee having a conversation with the human subject. Micro-expressions may also (or alternatively) be captured from that other person and analyzed, so that the effect of that's person's emotions can be determined relative to the human subject's emotions. In addition, the content of the dialogue may be captured (e.g., from a written script or plan, or from speech-to-text conversion) and analyzed, such as by capturing audio along with video that is used for the micro-expression analysis. Such audio may be converted to text, and such text may then be analyzed to determine topics of the conversation. Such topics may then be compared to the emotions exhibited by the human subject, as identified using the micro-expression analysis, to determine also the effect that particular words or topics have on the emotions of the human subject, or that the micro-expressions exhibited by one participant to the dialogue has on emotions of the other participant or participants. Great specificity may be obtained in the micro-expression analysis by using high-resolution video (so as to capture very small muscle movements) and high-speed video (so as to also capture small movements that may last for a very short time).

Figure 1:
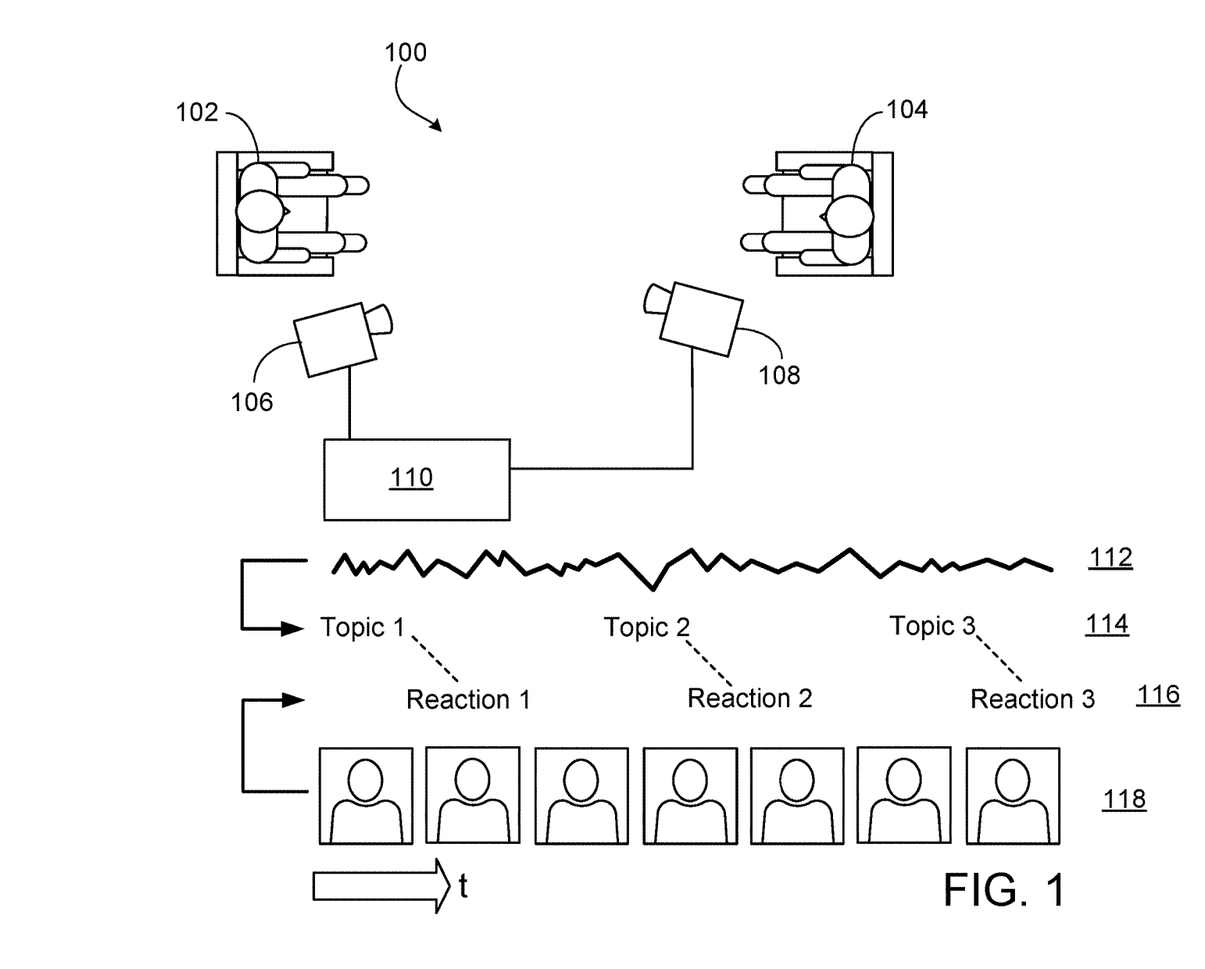
FIG. 1 is a conceptual diagram of a computerized emotion tracking system.

FIG. 1 is a conceptual diagram of a computerized emotion tracking system 100. In general, the system 100 captures digital video showing facial expressions of one or more humans involved in an information dialogue, and correlates emotions indicated by micro-expression analysis with topics of the information dialogue. For example, negative reactions—even when a human subject is trying to mask those reactions—may be correlated to a particular topic in the dialogue that occurred just before the relevant reactions, and that topic may subsequently be avoided or otherwise treated in a special manner, given the knowledge that it has previously had a negative effect on the subject. Similarly, when micro-expression analysis is performed on two subjects on opposed sides of the dialogue (e.g., an interviewer and interviewee, or a therapist and patient, or a moderator/person in video feed and each of multiple people in an audience who are individually analyzed for micro-expressions), the correlation between their emotions may be analyzed. For example, each subject may be classified by a computer system as being a talker or a listener at a particular time and their emotions (either as a deliverer of the message or the receiver of the message) may be determined using micro-expression analysis. Either alone or in combination with analysis of content of the communication, such micro-expression analysis may tell a researcher the sorts of effect that the talker's emotions have on the listener (and vice-versa). For example, a psychotherapist may learn that he or she is expressing emotions that he or she did not intend to express, and that such emotions are having a corresponding emotional effect on a patient. With such knowledge, the psychotherapist may alter his or her approach to therapy.

Referring now more specifically to FIG. 1, there is shown a system 100 in which a human subject 104 is interacting with another person 102. The term subject here is intended to indicate that the particular person is having micro-expression analysis performed on them, and in certain implementations both subject 104 and person 102 may be subjects who have micro-expression analysis performed on them. In other implementations, more than two subjects may be involved—whether with one person on one side of the dialogue and multiple subjects on the other (e.g., where the subjects are watching a video feed or speech), multiple persons on one side and one subject on the other, or multiple subjects on both side (e.g., in group discussions).

In this example, person 102 and subject 104 are seated and facing each other, having a verbal and visual dialogue with each other. For example, person 102 may be a job interviewer and subject 104 may be an interviewee, where the goal is to analyze the emotional effect that certain interviewing techniques have on a typical interviewee. The person 102 may be a subject of analysis when an attempt is made to discern the emotions the interviewer is conveying when he or she asks questions, or the emotions the interviewer faces when listening to answers from the interviewee. As another example, person 102 may be a therapist and subject 104 may be a patient, where the goal is to identify the emotions the patient feels when asked certain questions or lines of questions by the therapist, or to identify emotional cues the therapist may be giving off from his or her own micro-expressions. Such approaches may allow the therapist to better understand the mental state of the patient (because of the difficulty in hiding micro-expressions) and may also allow the therapist to better adjust his or her approach to providing therapy, such as by further pursuing certain lines of questioning when the micro-expression analysis indicates a positive response from the patient, and terminating or adjusting certain lines of questioning when the micro-expression analysis indicates a negative response.

In this example, a camera 106 is trained on the face of subject 104 and a camera 108 is trained on the face of person 102. Each camera may be high-definition (e.g., 1080P, 4K, or higher with a frame rate 60 fps, 120 fps, 240 fps, or higher). The cameras 106, 108 may each generate a digital signal and may provide their respective signals to an analysis system 110, which may take in those signals and other information to determine emotions of person 102 and subject 104 as they have a dialogue with each other. The cameras 106, 108 may also capture audio of the dialogue in the form of words spoken aloud by person 102 and subject 104.

In other implementations, person 102 may be a different participant in the dialogue, such as a video regarding a particular topic or topics. For example, a prerecorded or live video may be played to subject 104, who may be subjected to the video and whose reaction to the video may be captured. In such situations, camera 108 may capture the video such as by being aimed at a monitor on which the video is being played and at which the subject 104 is facing, or by the video stream being fed directly to system 110 as a digital signal. In some implementations, where the video stream shows the face of another person, micro-expression analysis may have been performed on that person at the time the video was captured, or may be performed later as the video is played, and such micro-expression data may be employed in the manners discussed above and below.

The remainder of FIG. 1 shows schematically the generation and use of certain types of metadata generated as part of the dialogue that occurs between person 102 and subject 104. As shown, signal 112 represents one or more parts of the video signal captured by camera 108. Such signal may include audio and video of person 102, including audio that captured words said by person 102, and video that captured facial expressions of person 102.

In this example, the signal 112 is analyzed to identify topics raised in the dialogue, such as by the person 102 speaking and their voice being captured by a microphone associated with camera 108. Such analysis may first involve speech-to-text conversion of the sounds captured by the camera 108. In certain situations, the language model that is used for such conversion may be a general model consistent with general word usage in the English (or other) language. In other situations, the language model may be a specialized model, such as a model directed to psychotherapeutic examination, e.g., so that words like "feel," "understand," and other such words are weighted more heavily as possible solutions for the speech-to-text conversion process than are other words that are known to be spoken less often in such an environment.

Content analysis may then be performed on the generated text to generate a string of topics 114, where each such generated topic may be correlated to a time in the dialogue, and thereby correlated to emotions determined form micro-expression analysis. Such analysis may be performed by parsing the text and identifying clustering of words that are not common (e.g., words other than a, an, the, and other such common parts of speech), and comparing such identified terms to models that identify discussion topics. For example, if the dialogue is a job interview, words like "challenge" or "bad" may be viewed as suggesting a topic in which the interviewer is challenging the interviewee to identify and discuss their failings. The generation of topics may occur continuously as the speech is converted to text, including by placing a sliding window on the text and repeatedly identifying topics for the text within the sliding window (e.g., of several seconds or more in width). A new topic label may be generated each time that the topical analysis on the sliding window identifies a topic that is sufficiently certain and sufficiently different than a prior topic so that it can be said that the topic of the dialogue has changed. The various topics (as represented by terms of one or more words) may then be stored and analyzed as metadata that results from the captured video signal.

Metadata may also be captured and generated from the video, such as video of subject 104 captured by camera 106. A series of video frames 118 is shown schematically here, and may show the state of the subject's face across small spans of time (such as one tenth of a second, one hundredth of a second, or less for each successive frame). Consecutive ones of the frames may have the subject in the frame (the person's face, e.g.) aligned with each other (to remove variability from the subject 104 moving his or her head), and zones of the subject's face may be identified, such as by analyzing pixels and groups of pixels that are similar in color to each other (so as to represent common features of the person's face across different frames over time). For example, the tip of the subject's nose will generally be represented by a small group of pixels that are relatively lighter in hue than the pixels around them. Changes in such pixels from frame-to-frame and across multiple groups of frames, may indicate motion of parts of the subject's 104 facial muscles relative to other parts of the face that did not move in the same manner. Where such motions are small and very fast (twitchy), they may be identified by the system 100 as being micro-expressions. In certain situations, such analysis may be performed by one or more software applications such as the FaceReader application from Noldus Information Technology of Leesburg, Va., USA and Wageningen, The Netherlands.

In this example, the output of such analysis is a string of "reactions" 116, which may be in the form of textual or numeric emotion labels that identify a correct emotional state of the subject 104 that is indicated by the micro-expression analysis. Also, as shown here, the reactions 116 are aligned in time with the topics 114, such as in a form of digital transcript of the dialogue session. Thus, a micro-expression identified a fraction of a second after the words that complete a topic are spoken may be determined to have resulted from the subject's reaction to those words and that topic. Similarly, emotions indicated by micro-expressions captured from the person delivering the message may also be captured and correlated to the topic delivered and to the other users reaction (again, where the correlation may involve aligning earlier activity by the person delivering the message with slightly later activity (e.g., about ½ to 1 second later or longer) from the person receiving the message—to account for the receiver's delay in appreciating what the message conveys (with in terms of its content, in terms of the delivering person's voice, and in terms of the delivering person's facial and/or body language captured by digital camera)

The system 100 may then correlate the reactions to the topics, and may make recommendations based on such analysis. For example, transcripts like those shown here—which at least correlate topics to reactions (and potentially to emotions of the creator of the message)—may have their data aggregated across a large number (100s or 1000s) of subjects, and conclusions may be made about how particular topics are perceived by members of the general population. In such situations, the same or similar dialogue input (e.g., by playing the same video to multiple subjects or reading the same script to the users) may be presented to various subjects so that the topics and the order of the topics is identical for all such subjects, and then the reaction labels for each such topic may be tallied and statistically analyzed. As noted above, the population for which micro-expression data has been obtained can have its statistics divided by various personal characteristics such as race, gender, age, and life experiences (e.g., as determined by surveying each participant).

In other implementations, the metadata shown in 116 and 118 may alternatively or additionally be generated for person 102. Such data may indicate emotions that result from something said by subject 104 and also emotions that the person 102 may be conveying visually toward subject 104. Such micro-expression analysis for person 102 may then be correlated time-wise to micro-expression analysis for subject 104, which may allow a researcher to better understand the effects of the person 102 and the subject 104 on each other, and particularly in the effect of the emotions of one person on the other person. The non-verbal interaction may be analyzed in terms of mirroring i.e., to what extent person 102 is mirroring different emotional expressions from person 104 and vice versa. This may be done by applying e.g., by using Granger causality analysis with different time lags. Fast mirroring bellow 300 ms may be seen as results of unconscious processes while mirroring above 500 ms may be the result of conscious cognitive processes. This data may also be used as measures of dominance and emotional attentiveness.

In yet other implementations, non-content-based analysis may alternatively or in addition be performed on the audio of the dialogue. For example, the amplitude of speech, the harshness of the speech, the speed of the speech, and the itch of the speech may be analyzed to identify an emotion of the speaker, and thus emotions to which the listener is being placed. Such additional metadata from the dialogue may be analyzed along with the emotional cues from the micro-expression analysis to determine the emotional effects that each such person is having on the other person. For example, such analysis may identify that a particular topic has a limited emotional effect on a listener when delivered in a relaxed manner, but a great emotional effect when delivered in a more urgent manner.

In this manner then, the system 100 can capture one or more video feeds from an ongoing dialogue that features a subject being studied and one or more partners to that dialogue. Such analysis may focus on micro-expression analysis so as to capture cues from a person that the person is not aware that they are giving off and that can be difficult for the person to block. Such cues may be used along with other cues in coordinating a message with the reaction of the person receiving the message so as to improve for the future the way that messages of such type are delivered.

Figure 2:
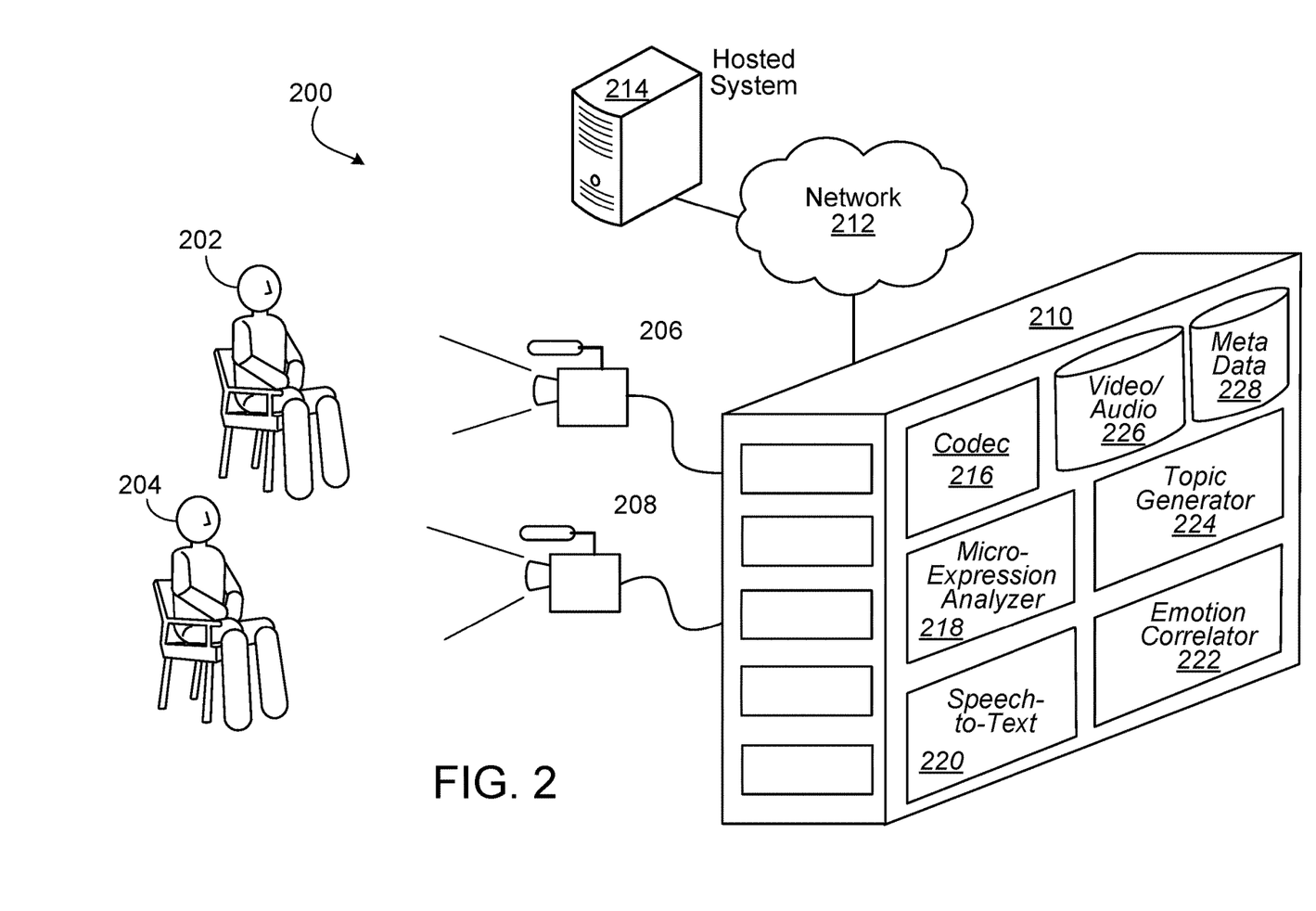
FIG. 2 is a schematic diagram of a system for analyzing micro-expression data.

FIG. 2 is a schematic diagram of a system 200 for analyzing micro-expression data. In general, the system 200 is similar to, and can be the same as, system 100 shown in FIG. 1. The system 200 shown here is depicted with more detail (as compared to FIG. 1) regarding the operation of an underlying analysis sub-system 210.

In the figure, a person 202 and a person 204 are shown. These may be two people who are having a verbal dialogue with each other. For example, they may be participants in a debate on a sports program or a political debate. They may be a therapist and patient. They may be a debater, and a member of the public watching the debate. They may be an interviewer and interviewee. They may alternatively be a teacher and a student, a supervisor and a supervisee, an investigator and a suspect or a witness, a recruiter and an applicant, a seller and a customer, or any appropriate kind of decision maker and employees. Generally, the persons 202 and 204 are located so that they can see and hear each other, either directly or via video feed, or at least so that one of them can see and hear the other.

Each of persons 202 and 204 are being recorded by digital video cameras 206 and 208, which capture high-resolution and high-speed video of each of persons 202 and 204, and also capture audio of the persons 202 and 204. Both such feeds may be captured and stored after the dialogue session is complete, or may be fed directly in real time to analysis sub-system 210, which may be a special-purpose computer system programmed to generate metadata from the captured video and to analyze such metadata The figure shows particular exemplary structures as part of the analysis sub-system 210 that may carry out the operations needed for such analysis from the captured video. The sub-system 210 is shown here as a rack server system to indicate that such processing may typically be performed by such a server system, though in various implementations, separate sub-systems at different locations may be employed, and various different types of specialized computers may be used.

In the sub-system 210, a codec 216 receives video signals from the cameras 206 and 208, and converts those signals, respectively, to digital information that may be analyzed in a variety of ways. For example, the codec may be employed to strip sample frames out of the video feed for analysis by other parts of the sub-system 210. Also, the codec 216 may extract one or more audio feeds captured by microphones with the cameras for such analysis.

A speech-to-text module 220 may obtain the audio portion of the extracted signal and may convert it to a string of text. Where there are multiple subjects to a dialogue, their spoken input may be captured by different microphones and used to generate different audio files or a single file (e.g., with textual designators setting off each respective participant, such as in a typical multi-party transcript). The speech-to-text module 220 may generate a string of text separately for each such speaker and may align and correlate those strings to each other so that it can be determined what statements by a first person were made in response to which statements by another person.

A micro-expression analyzer 218 may receive the video-only part of the feed from one or both of cameras 206 and 208 or from another video feed (e.g., a direct feed of a television program being watched by a person whose reactions are being subjected to micro-expression analysis). The analyzer 218 may take the form, for example, of the FaceReader application executing on one or more computer processors, which may be provided with a video file or stream of a person's face and may provide as an output one or more textual emotion labels that are keyed to particular times in the video file.

The structures discussed here may obtain the audio and video data from a video/audio database 226, which may store one or more files that have been captured by cameras 206 and 208 or by other mechanisms. The database 226 may store the files in familiar formats such as MOV, MP4, and other common formats. Also, multiple video and/or audio feeds may be correlated time-wise to each other, such as signals received from two different cameras trained on two different participants to the same dialogue session. In this manner, actions by one participant may be aligned in time with reactions by another participant.

The data generated by these structures and others discussed below may be output, saved into, and accessed from, metadata database 228. That database 228 may take a familiar flat file or relational database form. The metadata may be a first derivative of the initial video and audio data, such as a textual string generated from the audio of a dialogue session. The metadata may also be a further derivative of the recorded data, such as by processing the textual string to then identify topics discussed in the dialogue session.

Also shown as part of the sub-system 210 is a topic generator 224. As discussed above, such a generator 224 may take as input the textual string generated by the speech-to-text module 220, and may parse the text and compare clusters of terms in the text in order to identify topics or ideas addressed by particular parts of the text. Such action may involve passing a window of varying word length across the terms in the string of text and repeatedly generating candidate topics, and then testing the candidate topics to produce final topic labels for parts of the text. Those topics may also be labeled with times of the audio in the dialogue session that produced the relevant topical labels, so as to permit correlation of particular topics with other particular metadata such as particular micro-expression labels for video analyzed at about the same time as the topics (though perhaps delayed somewhat to address the delay between an action and a reaction by a human subject).

An emotion correlator 222 may then take as inputs any topic labels created by the topic generator 224 and emotion labels produced by the micro-expression analyzer 218, which may each be correlated with each other, such as by both being correlated to a common time baseline (with possibly an offset of several seconds or less to take into account the delay between an action by one person (e.g., as spoken words) and a reaction by another (e.g., as micro-expression output). In this manner, the emotion correlator 222 may determine what topics resulted in particular emotions being indicated in the face of a subject who was listening to the audio that carried the topics. In a similar manner, where multiple participants to a conversation or other dialogue session have their faces captured on video and their micro-expressions tracked, the relative emotion labels for each such participant at a particular time may be correlated. In certain situations, the emotion labels may be slightly offset in time. For example, the emotional label for a speaker may be selected to be in advance by a second or fraction of a second relative to an emotion label for a listener, under the assumption that there is some delay in the listener seeing the emotion of the speaker, and then reacting to it.

Various forms of analysis may be performed on such time-wise correlated emotion data. As one example, analyses of interactions over time may be used to identify how participants to a dialogue mirror the actions of other participants to the dialogue. Time series analyses may be performed by using a specific micro-expression as an anchor, from which, with a defined time-delay, the following reactions of the dialogue partners are analyzed. Such first micro-expression may be identified in advance, and a system may continually monitor micro-expressions from one or other participants until such type of micro-expression is identified. The system may then record the resulting reaction micro-expressions from other participants soon after (e.g., two seconds or less)

Analysis of patterns of more complex micro-expressions and affect expressions may also be performed. For example, the analysis may determine whether certain patterns of different affects are connected to specific micro-expressions. The non-verbal interaction between two or more participants to a dialogue may be analyzed in terms of mirroring i.e., to what extent one person is mirroring different emotional expressions from another person and vice versa. Such determinations may be made, e.g., by using Granger causality analysis with different time lags. Fast mirroring below 300 ms may be seen as results of unconscious processes while mirroring above 500 ms may be the result of conscious cognitive processes. To determine whether and where such mirroring exists, the existence of a new micro-expression label for one participant may be correlated to a new but slightly later label for another participant, and the time lapse between the expression for one and for the other may be identified. For multiple such instances, the participation action-reaction pair and corresponding delay may be logged for later analysis, including statistical analysis. This data may also be used as measures of dominance and emotional attentiveness.

The Granger causality test is a statistical test for determining whether a time series can be used for forecasting another time series. The purpose is to predict the future values of a time series using prior values of another time series. Based on a time series A, one assumes a "Granger-cause" to another time series B by a series of t-tests or/and F-test on lagged values of A. It is assumed that the A-values of the first time series give rise to statistically significant information about upcoming values in time series B. This causality relationship is based on two principles: (1) the cause is happening prior to an effect and (2) the cause has specific information about future values of its effect. In this manner, the correlations between causes (prior micro-expressions, words in a transcript, or topics generated from a transcript) and effects (micro-expressions captured from participants who are subjected to one or more of the causes) may be identified in a statistically-significant manner.

Figure 3:
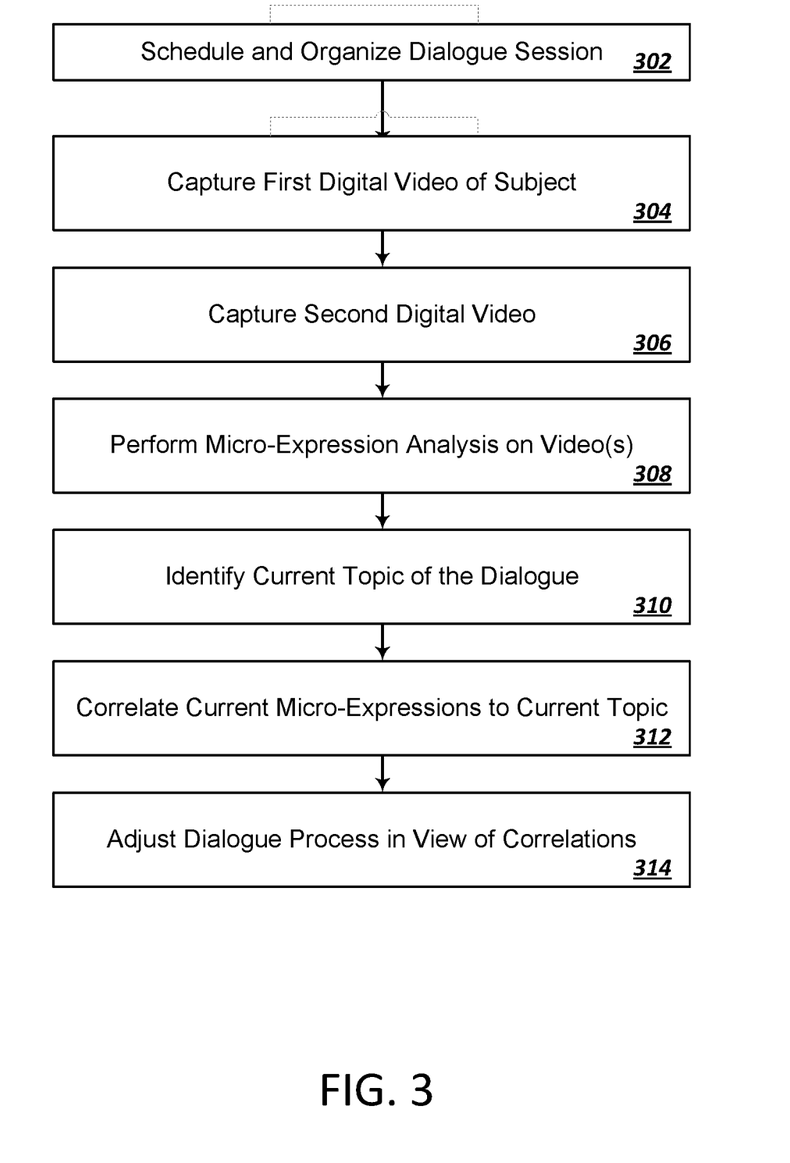
FIG. 3 is a flow chart of a process for identifying subject reactions in a captured video dialogue.

FIG. 3 is a flow chart of a process for identifying subject reactions in a captured video dialogue. In general, the process involves tracking, via captured digital video, meta-data about actions by participants to a dialogue, where the meta-data about one or both participants includes data generated from micro-expression analysis.

The process begins at box 302, where a dialogue session is scheduled and organized. The session may take a variety of forms, such as that of a viewer watching a video like a television program, movie, or advertisement(s); a potential employer interviewing a potential employee; a psychotherapist interacting with a patient; and other situations in which the hidden or expressed emotions of one or more participants to the dialogue may be desired to be tracked and analyzed.

At box 304, a first digital video may be captured of a human subject. Such capture may be of a continuous video across an entire dialogue session, including using high-resolution (e.g., 4K) and high speed (e.g., 60 to 240 frames per second). The video may be captured by a camera aimed at a face of the subject, at substantially a right angle to the subject's face so as to capture changes in muscle motion across the subject's entire face, including forehead, chin, and cheeks, and muscles around the eyes (to be distinguished from movement of the subject's eyeballs).

At box 306, a second digital video may be captured of another subject or of a video that is being used to interact with the human subject. Again, this video may be a high-resolution and high-speed video, particularly when it is video that captures the face of a second human subject.

Each of the captured videos may be saved separately or together in a single file, and in any event, may be coordinated timewise so that the portion of one video that was captured at a particular moment in time can be correlated to the same moment in time for the other video. The videos may also include one or more audio tracks, such as an audio track for each of the subjects in a person-to-person dialogue.

At box 308, micro-expression analysis is performed on one or more of the captured videos, where the respective analyzed videos are of the face of a human subject. Such analysis may result in numeric figures identifying the location of, amplitude of, and speed of, micro-changes in the faces of the video-captured subjects.

At box 310, a topic of the discussion or dialogue is identified. Such a topic may be identified in a variety of manners. For example, speech-to-text analysis may be performed when the discussion is spoken, and such generated text may be applied to a topic analyzer that may then apply a topical label to the portion of the dialogue at a particular point in time. Other labels may be generated for other points in time in the dialogue. For example, a different topical label may be applied every 10-30 seconds.

At box 312, the current micro-expression or micro-expressions may be correlated timewise to each other or to the generated topics of the conversation. For example, if a speaker said "How do you feel about your mother," the topical label may be "Freud" and the micro-expression may indicate a quick imperceptible twitch by the listener. The system may combine those two pieces of data to determine that such a micro-expression indicates discomfort, and thus that the listener has discomfort on Freud-related issues.

As another example, analysis of micro-expression data may be used to identify the presence in a participant, and in response to specific topics, to ambivalence or contradictive affects. Often emotional reactions are not ambiguous. When talking about a specific topic, person, or even product, different emotions could be expressed simultaneously. These emotions can be highly contradictive. The analysis described here can allow a computerized system and related researcher to identify these different emotions and can thus help to detect ambivalences or negative emotions (often expressed outside the awareness of the person as micro-affects). An interviewer who is presented during an interview with information that such micro-affects are occurring may subsequently confront the interviewee with the contradictive information, and the reaction of the interviewee may be observed when such confrontation occurs. It is of relevance how the interviewed person reacts. It is possible to detect a real surprise and an ongoing reflection on possible reasons, indicating some internal processing or, even more relevant, if the individual reacts as getting caught, e.g., with a fake smile, i.e., one corner of the mouth is lifted some milliseconds earlier than the other corner of the mouth (indicating a fake smile).

At box 314, the dialogue process is adjusted in view of the correlations. For example, when the process is being performed in real-time, such as for the benefit of a psychotherapist talking to a patient, a computer display that is visible to the therapist but not to the patient may generate a message indicating the patient's discomfort with the most recently-posed question or statement by the therapist. The therapist may use such feedback to further pursue the topic, but with due care that matches the emotion indicated by the micro-expression analysis and other judgments that the therapist may make (e.g., the therapist's understanding of the patient's ability to handle uncomfortable subjects). In other situation, a script may have been provided to multiple subjects, and the adjustment may come in the script, such as by changing the wording of a part of the script that micro-expression analysis indicates as drawing unwanted emotions out of people who hear the script read to them (e.g., in a commercial).

As another example, the efficacy of promotional messages may be tested using analysis from both sides of a promotional dialogue, where the first side may be a prerecorded promotional video with audio, and the second side is analysis of micro-expressions and other data from participants who are subjected to the promotional video and/or audio. The analysis described here may correlated which content and which wording in the promotional presentation is followed by which affective reactions of a viewer (or several viewers of a specific target group). Similarly, when developing the design of a web-site, a home page, or an app, users of such items may be subjected to micro-expression analysis as they are first presented with the items. The spontaneous affective reactions of customers are of high relevance to determining the effectiveness of such items or promotional messages. For example, how does a customer experience look like, not only on a conscious level, but on a level reflected in micro-expression analysis. As one example, when a customer comes to a specific web-site, does the internet-performance create interest and/or attention, or does a possible customer show signs of negative affectivity and how much interest is detectable.

Figure 4:
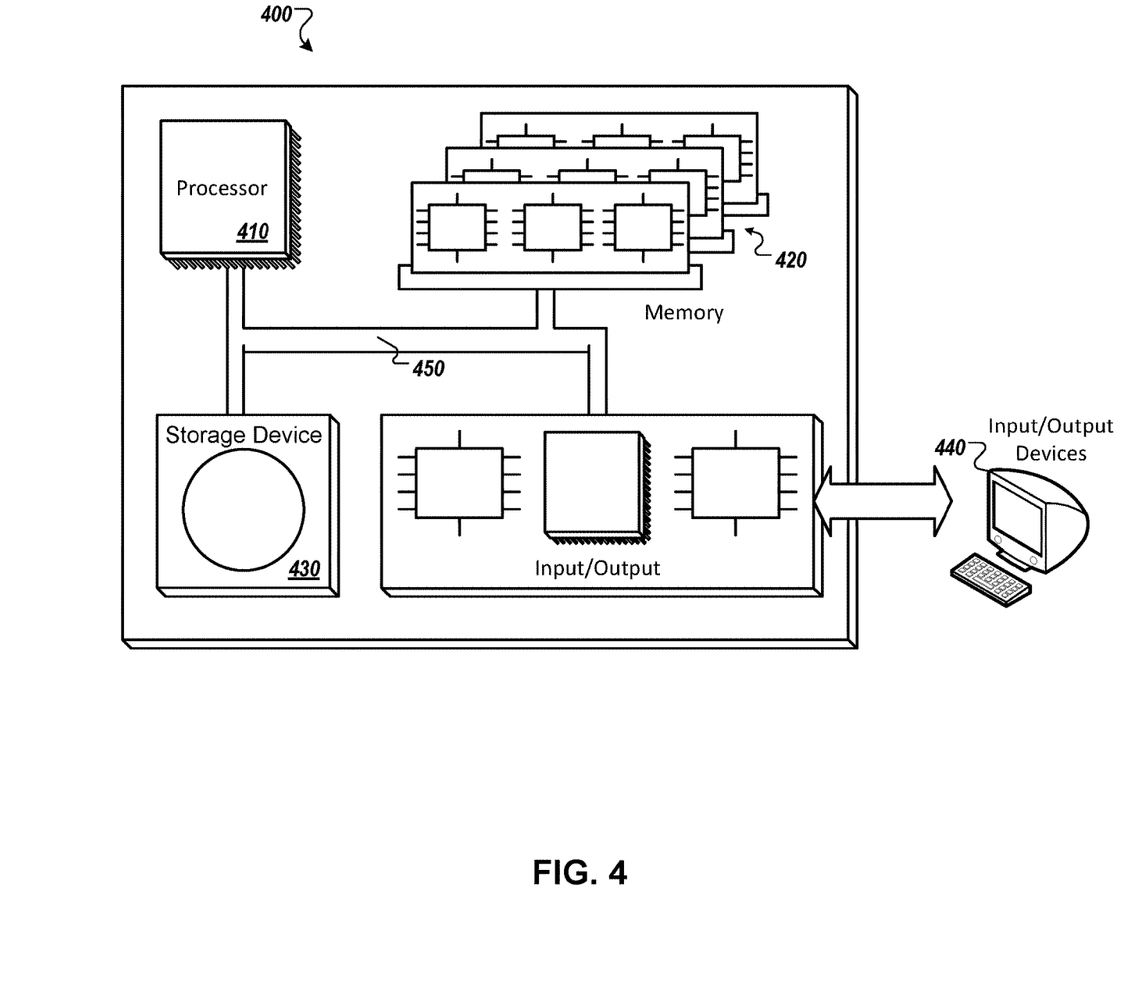
FIG. 4 shows an example computer system that can be used singularly or in multiples to carry out the techniques described herein.

FIG. 4 is a schematic diagram of a computer system 400. The system 400 can be used to carry out the operations described in association with any of the computer-implemented methods described previously, according to one implementation. The system 400 is intended to include various forms of digital computers, such as laptops, desktops, workstations, personal digital assistants, servers, blade servers, mainframes, and other appropriate computers. The system 400 can also include mobile devices, such as personal digital assistants, cellular telephones, smartphones, and other similar computing devices. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. The processor may be designed using any of a number of architectures. For example, the processor 410 may be a CISC (Complex Instruction Set Computers) processor, a RISC (Reduced Instruction Set Computer) processor, or a MISC (Minimal Instruction Set Computer) processor.

In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method of digital image analysis, the method comprising:
    identifying a topic of a portion of a presentation being provided to a human subject;
    obtaining first digital video of the human subject that indicates facial expressions of the human subject while the portion of the presentation is provided to the human subject;
    performing micro-expression analysis on the human subject using the first digital video;
    comparing results of the performed micro-expression analysis with the identified topic, and determining a reaction type of the human subject based on the micro-expression analysis with respect to a context of the topic; and
    modifying a manner of performing interaction with the human subject or other human subjects based on the comparing of results.

2. The computer-implemented method of claim 1, further comprising:
    obtaining second digital video of a presentation with which the human subject was interacting when the first digital video was captured; and
    time-wise aligning data generated from the second digital video with the results of performing the micro-expression analysis, so that particular ones of the results of performing the micro-expression analysis are correlated with particular messages delivered by the presentation to the human subject.

3. The computer-implemented method of claim 2, wherein the presentation with which the human subject interacts is a conversation with another human.

4. The computer-implemented method of claim 3, further comprising electronically converting speech by the another human to text for computer analysis.

5. The computer-implemented method of claim 4, further comprising electronically identifying one or more topics to which text from speech of the another human is determined to be directed.

6. The computer-implemented method of claim 5, further comprising electronically correlating each of the identified one or more topics to corresponding emotion tags identified from the micro-expression analysis that indicate emotional reactions of the human subject to the one or more topics.

7. The computer-implemented method of claim 1, wherein modifying a manner of performing interaction comprises modifying a manner of interaction with a person other than the human subject.

8. The computer-implemented method of claim 1, wherein identifying a topic of a portion of a presentation being provided to a human subject is performed by performing automatic speech-to-text analysis of the presentation.

9. The computer-implemented method of claim 1, wherein identifying a topic of a portion of a presentation being provided to a human subject comprises receiving a menu selection from a person who is interacting with the human subject.

10. The computer-implemented method of claim 1, wherein the micro-expression analysis comprises analysis of motion of the human subject's skin.

11. A device having tangible, non-transitory machine-readable storage, having instructions that when executed by one or more processors, perform operations comprising:
    identifying a topic of a portion of a presentation being provided to a human subject;
    obtaining first digital video of the human subject that indicates facial expressions of the human subject while the portion of the presentation is provided to the human subject;
    performing micro-expression analysis on the human subject using the first digital video;
    comparing results of the performed micro-expression analysis with the identified topic, and determining a reaction type of the human subject based on the micro-expression analysis with respect to a context of the topic; and
    modifying a manner of performing interaction with the human subject or other human subjects based on the comparing of results.

12. The device claim 11, wherein the operations further comprise:
    obtaining second digital video of a presentation with which the human subject was interacting when the first digital video was captured; and
    time-wise aligning data generated from the second digital video with the results of performing the micro-expression analysis, so that particular ones of the results of performing the micro-expression analysis are correlated with particular messages delivered by the presentation to the human subject.

13. The device of claim 12, wherein the presentation with which the human subject interacts is a conversation with another human.

14. The device of claim 13, wherein the operations further comprise electronically converting speech by the another human to text for computer analysis.

15. The device of claim 14, wherein the operations further comprise electronically identifying one or more topics to which text from speech of the another human is determined to be directed.

16. The device of claim 15, wherein the operations further comprising electronically correlating each of the identified one or more topics to corresponding emotion tags identified from the micro-expression analysis that indicate emotional reactions of the human subject to the one or more topics.

17. The device of claim 11, wherein modifying a manner of performing interaction comprises modifying a manner of interaction with a person other than the human subject.

18. The device of claim 11, wherein identifying a topic of a portion of a presentation being provided to a human subject is performed by performing automatic speech-to-text analysis of the presentation.

19. The device of claim 11, wherein identifying a topic of a portion of a presentation being provided to a human subject comprises receiving a menu selection from a person who is interacting with the human subject.

20. The device of claim 11, wherein the micro-expression analysis comprises analysis of motion of the human subject's skin.

* * * * *